(12) United States Patent
Kogan

(10) Patent No.: US 9,636,454 B2
(45) Date of Patent: May 2, 2017

(54) ELECTRICAL SAFETY METHODS, DEVICES, AND SYSTEMS FOR MEDICAL TREATMENT DEVICES

(75) Inventor: Yakov Kogan, Bedford, MA (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 346 days.

(21) Appl. No.: 14/123,066

(22) PCT Filed: Jun. 8, 2012

(86) PCT No.: PCT/US2012/041740
§ 371 (c)(1),
(2), (4) Date: Apr. 21, 2014

(87) PCT Pub. No.: WO2012/170942
PCT Pub. Date: Dec. 13, 2012

(65) Prior Publication Data
US 2014/0228803 A1    Aug. 14, 2014

Related U.S. Application Data

(60) Provisional application No. 61/590,409, filed on Jan. 25, 2012, provisional application No. 61/494,770, filed on Jun. 8, 2011.

(51) Int. Cl.
*A61M 5/00*     (2006.01)
*A61M 5/168*    (2006.01)
*A61N 1/08*     (2006.01)
*A61M 5/50*     (2006.01)

(52) U.S. Cl.
CPC ...... *A61M 5/16831* (2013.01); *A61M 5/5086* (2013.01); *A61N 1/08* (2013.01)

(58) Field of Classification Search
CPC .... A61M 5/16831; A61M 5/5086; A61N 1/08
See application file for complete search history.

(56) References Cited

U.S. PATENT DOCUMENTS

| | | | |
|---|---|---|---|
| 8,777,887 B2* | 7/2014 | Jonsson | A61M 1/16 128/908 |
| 2005/0267698 A1 | 12/2005 | Gordon | |
| 2006/0030917 A1 | 2/2006 | Eccleston et al. | |
| 2007/0095400 A1* | 5/2007 | Bergquist | F16K 7/14 137/485 |
| 2010/0312161 A1 | 12/2010 | Jonsson et al. | |

FOREIGN PATENT DOCUMENTS

EP    1623733    2/2006

OTHER PUBLICATIONS

International Search Report and Written Opinion for International Application No. PCT/US12/41740, dated Aug. 10, 2012.

* cited by examiner

*Primary Examiner* — Amanda Patton
(74) *Attorney, Agent, or Firm* — Potomac Law Group, PLLC; Mark Catan

(57) ABSTRACT

Systems, methods, and devices can detect a dangerous or adverse condition or anticipated condition that indicates an undesirable amount of electric current in a patient-connected tube providing fluid to a patient. The fluid flow to the patient is stopped responsive to the detection. Stoppage of fluid flow to the patient can reduce or prevent electric current in the fluid from reaching a patient, flowing through the patient to ground, and/or continuing to flow through the patient.

25 Claims, 7 Drawing Sheets

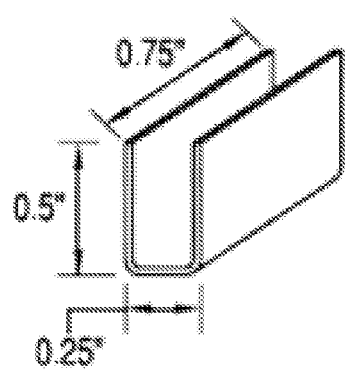 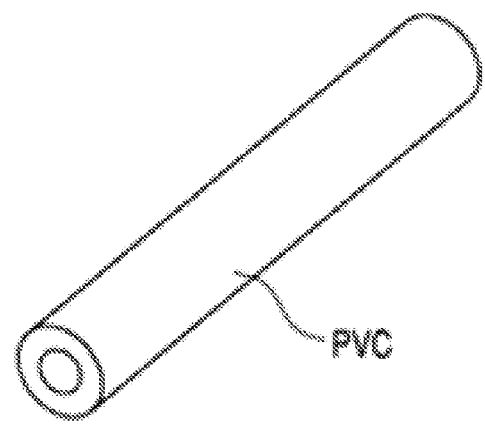
*FIG. 6A*        *FIG. 6B*

ELECTRICAL SAFETY METHODS, DEVICES, AND SYSTEMS FOR MEDICAL TREATMENT DEVICES

CROSS-REFERENCE TO RELATED APPLICATIONS

The present application is a U.S. national stage entry of International Application No. PCT/US12/41740 filed Jun. 8, 2012, which claims the benefit of U.S. Provisional Patent Application No. 61/494,770 filed Jun. 8, 2011 and U.S. Provisional Patent Application No. 61/590,409 filed Jan. 25, 2012, all of which are incorporated herein by reference in their entireties.

FIELD

The disclosed subject matter involves electrical safety methods, devices, and systems for medical treatment devices, and more particularly deals with systems, methods, and apparatuses that prevent and/or stop electric current from flowing from medical electrical ("ME") equipment to a patient connected to the medical electrical equipment.

BACKGROUND

The use of electrically powered medical devices or equipment (ME) connected to a patient is very common in modern medicine. Along with the benefits these devices are designed to bring to a patient, they also can create a potential hazard of electric shock to the patient. Electric shock can be caused by leakage current flowing through the patient's heart, for instance, creating ventricular defibrillation, which a medical device may induce in an earthed patient or sink to earth if the patient is in contact with another source of electricity. Electrical medical equipment standards are developed to minimize this hazard by specifying safe levels of patient leakage current flowing through patient applied parts of medical devices in no fault and specific fault conditions.

Accordingly, prevention and protection against electrical shock or leakage currents is a significant consideration in the design of medical electrical equipment. Leakage currents for medical electrical equipment may be defined by the path current takes and can include earth leakage current, enclosure leakage current (or touch current), patient leakage current, patient auxiliary leakage current, and mains voltage to applied part leakage current.

Most medical electrical equipment or devices have contact with a device operator, a patient, or both. Though leakage currents typically are small, the amount of current required to produce adverse physiological effects on a human body is also small, so such leakage currents must be limited to safe values by the design of medical electrical equipment. Accordingly, medical electrical devices must be designed to pass certain tests to ensure that excessive leakage current does not dissipate from the mains, the device enclosure, or applied parts to and through a human body. Portions of Standard ANSI/AAMI/IEC 60601, for instance, address safety requirements for medical electrical equipment.

Medical electrical equipment has a designated class and type, with categorization into class being based on the form of protection used against electrical shock or leakage current and type designation being defined by the degree of protection from electrical shock or leakage current.

Class I medical electrical equipment has a protective earth connection. The primary means of protection for Class I medical electrical equipment is the insulation between "live" parts and exposed conductive parts, such as a metallic enclosure. Supplemental protection is provided by the protective earth connection. Fault or leakage current can flow from the mains to earth via the protective earth conductive connection, which causes a protective device (e.g., a circuit breaker or a fuse) to disconnect the medical electrical equipment from the supply. Note, of course, that not all medical electrical equipment having a protective earth connection necessarily is classified as Class I medical electrical equipment.

Class II medical electrical equipment, on the other hand, does not have a protective earth, and protection against electrical shock is provided by reinforced insulation or double insulation. For double insulation, primary protection is provided by a first layer of insulation (including air) and secondary protection is provided by a second insulation layer. Leakage current can flow from Class II medical electrical equipment.

Different types of medical electrical equipment include B, BF, and CF, with each type affording a different degree of protection against electrical shock or leakage current. Generally speaking, B is for medical electrical equipment providing a particular degree of protection against electrical shock, particularly regarding allowable leakage currents and reliability of the protective earth connection (if present). BF is as type B, but with isolated or floating (F-type) applied part or parts. CF provides a higher degree of protection against electrical shock than BF, particularly with regard to allowable leakage currents and has floating applied parts. Incidentally, an applied part may be defined as a part of the medical electrical equipment which in normal use necessarily comes into physical contact with the patient for the equipment to perform its function or can be brought into contact with the patient or needs to be touched by the patient.

SUMMARY

The Summary describes and identifies features of some embodiments. It is presented as a convenient summary of some embodiments, but not all. Further the Summary does not necessarily identify critical or essential features of the embodiments, inventions, or claims.

Generally speaking, embodiments of the disclosed subject matter include systems, methods, and devices that can detect a medical electrical apparatus fault or an external fault that can potentially cause or has caused an increase in patient leakage current flowing in a non-conductive tube or tubes respectively filled with conductive liquid connecting a patient to the medical electrical apparatus, and responsive to the detection, mechanically break the continuity of the fluid in the tube or tubes. Such breaking of continuity can interrupt or prevent the passage of patient leakage current and thus stop or prevent electric shock to the patient.

Included among embodiments described herein are a method for protecting a patient from an electrical source, comprising: connecting the patient to a treatment device by a fluid line; receiving a voltage or current signal indicating a flow of current or voltage in the fluid line connected to the patient; determining if the voltage or current exceeds a predetermined threshold; and in response to the determining, closing a valve to break continuity between the patient and the treatment device. In various embodiments, a human perceptible output indicating the detected voltage or current may be generated.

Also, in embodiments, a system for protecting a patient from an electrical source, comprising: means for receiving a voltage or current signal indicating a flow of current or voltage in a fluid line connected to the patient; means for determining if the voltage or current exceeds a predetermined threshold; and means for closing a valve to break continuity between the patient and the treatment device in response to the determined voltage or current. Optionally, the system may further comprise means for generating a human perceptible output indicating the detected voltage or current.

Embodiments also include a system for stopping flow of a conductive fluid to a patient, comprising: means for identifying an unsatisfactory condition in the system indicative of patient leakage current or anticipated patient leakage current of an unacceptable amount; means for stopping fluid continuity to the patient based on the identified unsatisfactory condition. Optionally, the means for stopping the fluid flow continuity to the patient mechanically interrupts the fluid conductive path to the patient. Further, the means for stopping the fluid flow continuity to the patient can include one or more of a pinching apparatus that pinches closed a corresponding fluid flow line, a valve to break continuity between patient and a treatment device, a folding apparatus to fold the tube to close the corresponding fluid flow line, and a bubble introducing apparatus to introduce air into the fluid flow line to form an air break. Optionally or alternatively, the means for stopping the fluid flow continuity to the patient includes a valve to divert flow to a circuit having an air break. The circuit may have a drip chamber. The system can also comprise means for handling fluid coupled to the patient via one or more patient fluid flow lines, wherein normal operation of the fluid handling means can be interrupted responsively to the unsatisfactory condition indication. Optionally, the means for stopping fluid continuity to the patient may include redundant devices of same or different types for stopping fluid continuity. Further, stopping fluid continuity to the patient can prevent or stop electric shock to the patient.

In one or more embodiments, the unsatisfactory condition can be one or more of a sensed patient leakage current exceeding a predetermined amount, a sensed voltage differential associated with the patient leakage current exceeding a predetermined amount, a fault condition, an anticipated fault condition, a sensed change in fluid conductivity, a loss of earth, and vibration. Optionally, the unsatisfactory condition indication may be predictive of a harmful, dangerous, or adverse situation to the patient.

Optionally, the fluid continuity may be temporarily interrupted without shutting down means for supplying conductive fluid to the patient, wherein, once the unsatisfactory condition is resolved, the fluid continuity to the patient can be restored. Further, the system may be operative to stop fluid continuity to the patient when a fluid treatment machine thereof sinks to earth patient leakage current caused by external voltage applied to the patient.

In one or more embodiments, the acceptable amount of patient leakage current is zero. Alternatively, the acceptable amount of patient leakage current is 10 µA or below or below 10 µA. Optionally, the means for stopping fluid continuity to the patient causes reduction of patient leakage current to keep within or reduce to an acceptable limit.

In one or more embodiments, optionally, the means for identifying an unsatisfactory condition in the system includes one or more of at least one sensor disposed external to means for handling fluid and operative to sense a characteristic of a fluid line providing the conductive fluid to the patient; at least one sensor disposed internal to the means for handling fluid and operative to sense a characteristic of said means for handling fluid indicative of patient leakage current or an anticipated occurrence of patient leakage current; and at least one sensor disposed on or in association with the patient to sense indications of patient leakage current or an anticipated occurrence of patient leakage current.

Embodiments also can include a method for preventing or minimizing patient leakage current, comprising: identifying an indication of patient leakage current or a precursor to an unacceptable leakage current situation; and making discontinuous a fluid path to a patient responsive to said identifying.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Any values dimensions illustrated in the accompanying graphs and figures are for illustration purposes only and may not represent actual or preferred values or dimensions. Where applicable, some features may not be illustrated to assist in the description of underlying features.

FIG. 6A shows a portion of a sensor according embodiments of the disclosed subject matter.

FIG. 6B shows another portion of a sensor according to embodiments of the disclosed subject matter.

DETAILED DESCRIPTION

Figure 1A:
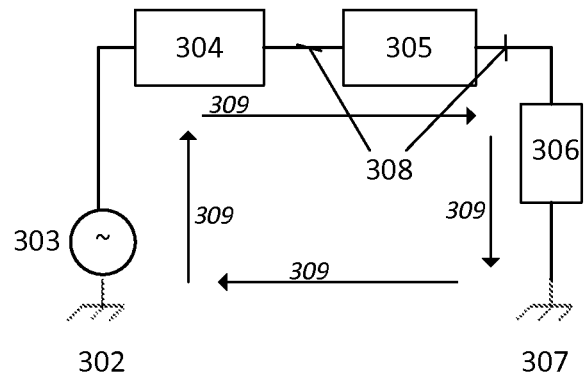
FIG. 1A is a schematic representation of patient leakage current in a medical system where an internal electrical or power source causes the patient leakage current.

The detailed description set forth below in connection with the appended drawings is intended as a description of various embodiments of the disclosed subject matter and is not intended to represent the only embodiments in which the disclosed subject matter may be practiced. The detailed description includes specific details for the purpose of providing a thorough understanding of the disclosed subject matter. However, it will be apparent to those skilled in the art that the disclosed subject matter may be practiced without these specific details. In some instances, well-known structures and components are shown in block diagram form in order to avoid obscuring the concepts of the disclosed subject matter.

Generally, an aim of one or more embodiments of the disclosed subject matter is to prevent and/or stop unwanted electric current flow (e.g., any current or current above a specified threshold) through a patient via conductive fluid connections between the patient and the medical electrical fluid handling equipment.

Medical electrical equipment or systems may be connected to a patient by one or more non-conductive tubes filled with conductive fluid. Some examples of such equipment or systems include infusion pumps, intravenous pumps, dialysis machines, medical fluid warmers, extracorporeal blood treatment, surgical red blood cell saving, introoperative and post-operative vacuum suction, and donor apheresis machines. The non-conductive tubes connecting these machines to a patient under treatment may become conductors of electricity, especially in the case where the fluids in the tubes have a significant concentration of dissolved ionic species. In some instances, these tubes may be the only electrically conductive connection between the patient and the medical electrical equipment, for example, where the connection to the patient applied part, such as intravenous needle or catheter, is represented by non-conductive tubes filled with conductive fluid creating a path for the patient leakage current. The tubes can couple voltage induced to the fluid from the medical electrical equipment to the patient. If the patient is connected to a grounded hospital bed or any other conductive apparatus, for instance, thereby closing the circuit, potentially harmful electric current can flow through the patient.

Another potentially dangerous situation can exist when a patient connected to a fluid handling medical device with tubes that are filled with conductive liquid is subject to the influence of an external voltage source, such as a malfunctioning electrical utility device. In such a case, the fluid handling medical device may close the electric circuit by coupling the conductive fluid flowing through the device to the AC Mains ground feeding it. The current flowing through the patient in the above described situations is known as patient leakage current, with allowable patient leakage current values being specified by national and international standards for medical electrical equipment (as discussed above).

Medical fluid handling apparatus functional requirements can dictate the design configurations which may create electrical coupling between a device's electric circuitry and physiological and treatment fluids. In some instances a medical fluid handling apparatus may be required to provide the fluidic path sterility. To achieve this frequently the fluidic path comprises a sterile disposable, constructed from hard plastic parts and tubing, for instance. These materials are usually good electrical isolators so energy transfer between fluid flowing in the machine and the machine circuitry is frequently only a result of capacitive or inductive coupling.

Embodiments of the disclosed subject matter include systems, methods, and devices that can detect medical electrical apparatus fault(s) and/or external fault(s) that potentially can cause or has/have caused patient leakage current or an unacceptable increase in or amount of patient leakage current flowing in a non-conductive tube or tubes respectively filled with conductive liquid connecting a patient to the medical electrical apparatus. Responsive to the detection, fluid flow to the patient can be temporarily interrupted, thereby preventing or stopping patient leakage current and preventing or stopping electric shock to the patient.

In one or more embodiments of the disclosed subject matter, normal operation of fluid handling equipment is interrupted upon sensing or detection of patient leakage current. Optionally or alternatively, normal operation of fluid handling equipment is interrupted upon detection of a potentially adverse or dangerous condition that most likely has led, may lead, or will lead to creation of patient leakage current. Once the adverse or dangerous condition is resolved, normal operation of the fluid handling equipment may resume. Interruption of normal operation can mean stopping fluid flow to a patient, but not necessarily shutting down or shutting down completely the fluid handling equipment. Stopping fluid flow to the patient can include one or more of breaking continuity in the fluid line and diverting fluid away from the patient as discussed herein. Examples of adverse or dangerous or potentially adverse or dangerous conditions can include an overcurrent, an undercurrent, a change in liquid conductivity, loss of earth, motor vibration, etc.

In one or more embodiments of the disclosed subject matter, an electric current flow in a non-conductive tube filled with conductive liquid can be sensed, detected, or otherwise identified, and said current can be reduced or interrupted by mechanically breaking the continuity of the fluid in the tube. For example, this can be accomplished in one or more embodiments, by closing a valve, pinching off the tube, or folding the tube. Additional non-limiting examples are set forth herein. In medical applications it may be preferable to use a pinch valve for this purpose to avoid introduction of wetted components into the flow passage, for example. Such mechanical breaking of continuity can electrically isolate the inlet and outlet fluid volumes.

Breaking continuity of a fluid flow tube (or line) to prevent electric current flowing through to the patient can be advantageous because the fluidic lines may be the only electrical conductors connecting a medical fluid handling electrical device to a patient under treatment. As set forth herein, other ways may be employed to handle patient leakage current. For example, optionally or alternatively, the fluid flow can be rerouted from the patient.

Breaking continuity of a conductive flow or rerouting the conductive flow from the patient may be a preferred way to prevent patient electrical shock as opposed to shutting down the machine partially or entirely. Reasons can include: (1) shutting down the machine or apparatus may not remove the hazard of electric shock to the patient. An example of this is when a medical machine or apparatus sinks to earth patient leakage current caused by external voltage applied to the patient; (2) it may be beneficial not to shut down completely the medical machine or apparatus so patient treatment can be quickly resumed without restarting the machine once the fault condition is removed.

As indicated above, breakage of the conductive fluid path can be triggered by one or more of a measured voltage, current, and fluid conductivity in the tube, for instance. One or more of such measurements can be taken proximate the tube. Thus, embodiments of the disclosed subject matter also can include one or more voltage detection sensors and/or one or more current detection sensors to provide protection against the electrical hazard described above. That is, the corresponding sensor(s) can be arranged proximate the tube. Note also that the trigger does not necessarily need to be voltage, current, or fluid conductivity. Further, one or more sensors as set forth herein can be elsewhere on a medical machine and/or on the patient. Modifying circuits can be electrically coupled to the sensor(s) and may control the mechanical "closing" apparatus (e.g., a valve, a pinch, etc.), such that it closes, once a possibility of potentially dangerous patient leakage current increase is detected or in-fact occurs.

Further, embodiments of the disclosed subject matter can also implement means to reduce patient leakage current to acceptable limits, such as isolated electrical AC/DC and/or DC/DC power supplies to reduce the electrical voltage induced to the isolated section of the supplies. Isolated power supplies can be employed to prevent unwanted patient leakage currents (e.g., any current or current above a specified threshold). Detection and shutoff circuitry and methods can also protect against leakage current when external voltage is applied to the patient.

Additionally, one or more embodiments of the disclosed subject matter can reduce patient leakage current to an acceptable limit. Such reduction can be implemented using one or more air gap fluid handling devices or apparatuses, for example, included in the medical electrical apparatus fluidic path. Air gap fluid handling devices can be employed to prevent unwanted patient leakage currents (e.g., any current or currents above a specified threshold) flowing from the parts of the system (or a portion thereof, such as a device, machine, or apparatus) that require the application of electrical signal to the fluid and/or have a strong parasitic coupling to any electrical signals within the medical apparatus due to its design dictated by functional requirements, for instance. Detection and shutoff circuitry and methods thereof can be used to provide protection redundancy and/or to supplement protection provided by air gap devices.

According to embodiments of the disclosed subject matter, normal operation of fluid handling medical equipment is interrupted responsively to over current or an over voltage condition or an indication that such a condition is imminent or likely at a future time and resumed once the condition or risk of the condition arising ends or falls below an acceptable threshold level.

According to further embodiments of the disclosed subject matter, an electric current flow in a non-conductive tube filled with conductive liquid may be reduced or interrupted by mechanically breaking the continuity of the fluid in the tube. For example, this can be accomplished in embodiments, by closing a valve, pinching off the tube, folding the tube, introducing air into the tube to form an air break, diverting flow to a circuit having an air break (such as a drip chamber), or other ameliorative device.

In practical applications for medical applications it may be preferable to use a pinch valve for this purpose for a variety of reasons, including, convenient control, cost, and because it avoids the need for additional wetted components in the flow passage. Such mechanical breaking of continuity is effective for electrically isolating the ends of a fluid circuit broken by such a pinch clamp.

Figure 1B:
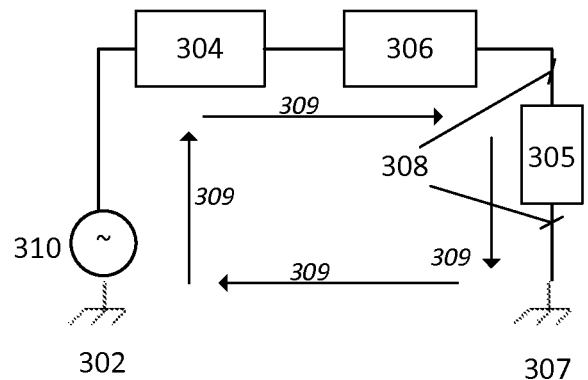
FIG. 1B is a schematic representation of patient leakage current in a medical system where an external electrical or power source causes the patient leakage current.

FIG. 1A shows a schematic representation associated with a patient leakage current path when the patient is earthed, through a hospital bed, for instance, and voltage is induced in the fluid via parasitic electric coupling between the fluid flowing inside the medical apparatus and current carrying parts of this apparatus. FIG. 1B shows a schematic representation associated with a patient leakage current path when the patient is touching an external source of electricity and the medical device sinks current to earth.

According to IEC 60601 Standard, for instance, the patient leakage current through patient applied part(s) located close to a patient's heart should not exceed 10 μA in no-fault and 50 μA in a fault condition. In one or more embodiments of the disclosed subject matter, it is desirable to detect these levels of current flowing through conductive fluid inside a non-conductive tube. Coupling impedance Zcoupling between the conductive fluid and the medical apparatus is usually high. This impedance can be treated as a shunt resistor to detect patient leakage current by measuring the voltage drop across Zcoupling, ΔVcoupling, as shown on FIGS. 1A and 1B, created by this current. The current measurement may be replaced by a differential voltage measurement. The voltage levels are usually relatively high due to the Zcoupling high values. As can be seen from FIGS. 1A and 1B the same differential voltage measurement will work for both cases.

Referring to FIG. 1A, the patient leakage current path 309 includes earth (i.e., ground) 302; a power or electrical supply 303 of a medical machine or apparatus (i.e., an internal power supply); the medical machine or apparatus, which is represented by its impedance 304 (Z source); a coupling impedance 305 (Z coupling) associated with an output of the power supply 303, typically the capacitive coupling between the fluid flowing inside of the medical machine or apparatus and parts of the medical machine or apparatus conducting or cable of conducting electricity; the patient, which is represented by impedance 306 (Z patient); and then to ground 307. Ground 307 can represent the patient's "earthed" condition, for instance through a hospital bed as indicated above. Voltage is induced in the fluid via parasitic electric coupling between the fluid flowing inside the medical apparatus line and current carrying parts of this machine. Ground 302 and 307 can be the same earth ground. A voltage difference 308 for the coupling impedance 305 is indicated (ΔVcoupling).

Referring to FIG. 1B, the patient leakage current path 309 includes earth (i.e., ground) 302; an external power or electrical supply 310; the medical machine or apparatus, which is represented by its impedance 304 (Z source); the patient, which is represented by impedance 306 (Z patient); a coupling impedance 305 (Z coupling); and ground 307, which can represent an external power supply. External power supply 310 may be from a broken utility device, for instance. In FIG. 1B, a power source inside the medical machine or apparatus in not inducing patient leakage current. A voltage difference 308 for the coupling impedance 305 is indicated (ΔVcoupling).

Figure 2A:
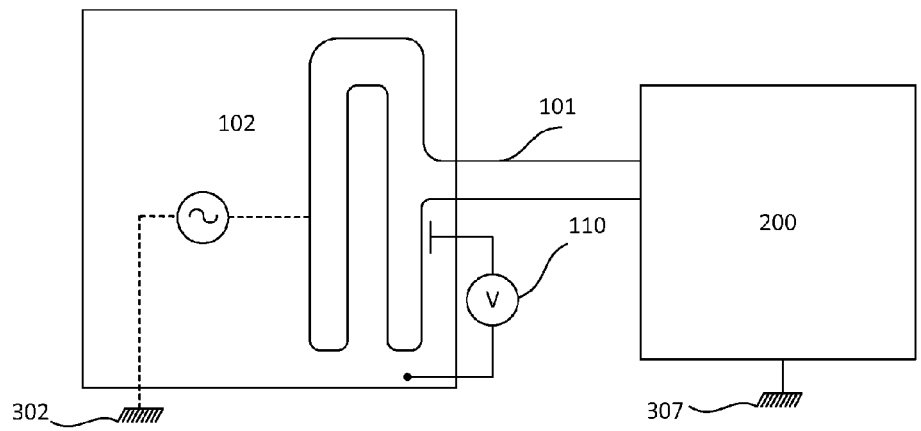
FIG. 2A is a diagrammatic representation of the schematic representation of FIG. 1A.
Figure 2B:
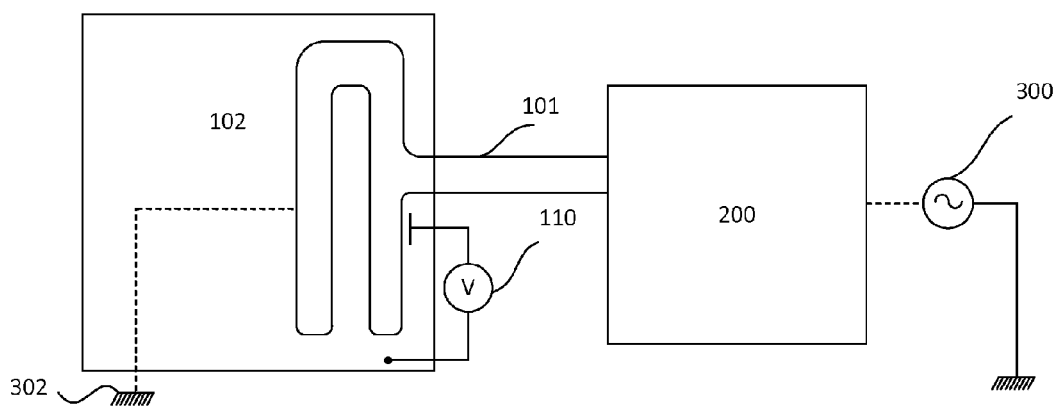
FIG. 2B is a diagrammatic representation of the schematic representation of FIG. 1B.

FIGS. 2A and 2B show different diagrammatic representations of systems, methods, and devices for sensing or detecting patient leakage current to patient 200 fluidly connected to treatment machine 102 via fluid path 101 under differing circumstances. FIG. 2A is represented schematically by FIG. 1A, and FIG. 2B is represented schematically by FIG. 1B. Circumstances caused by a voltage from machine 102 being coupled to the fluid line 101 (e.g., FIG. 2A), and circumstances caused by a voltage 300 external to machine 102 coupled to fluid line 101 (e.g., FIG. 2B). FIGS. 2A and 2BC include a voltage sensor 110, though as discussed herein embodiments are not limited to voltage sensors.

Figure 3:
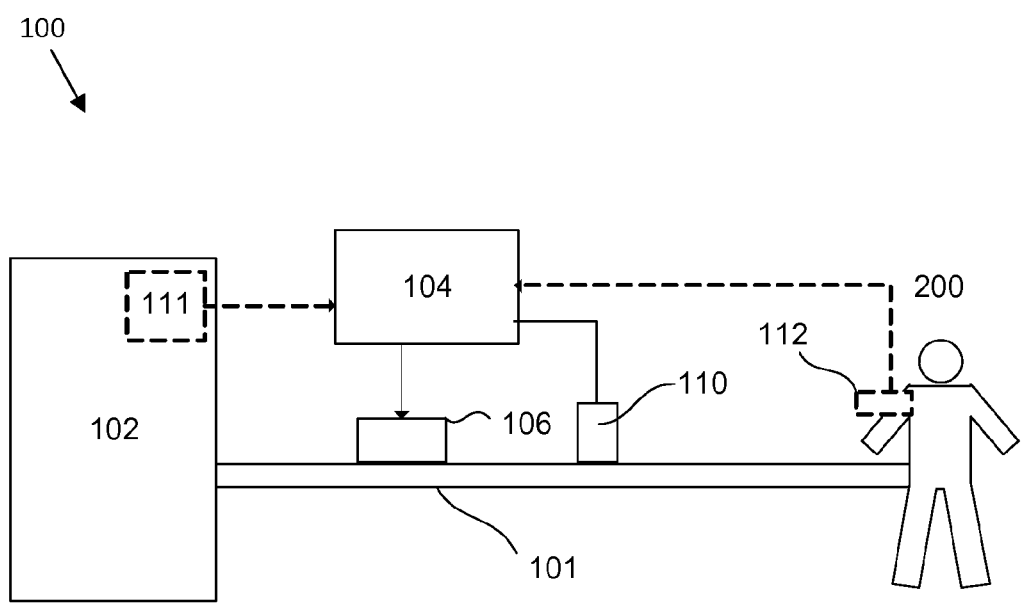
FIG. 3 is a block diagram of a system according to embodiments of the disclosed subject matter.

FIG. 3 is a block diagram of a system 100 according to embodiments of the disclosed subject matter.

The system 100 includes a treatment device 102, a controller 104 (e.g., a microprocessor, ASIC, FPGA, etc.), an electro-mechanical means 106 (e.g., a valve, a pinch, a fluid rerouting apparatus), a non-electrically conductive fluid conductor 101 (e.g., plastic tubing), and a sensing element 110 (e.g., a non-invasive capacitive voltage or current sensor). The fluid conductor 101 may be physically coupled to a patient 200 via a cannula, for example (not explicitly shown).

The sensor 110 can measure or detect signals associated with the flow of conductive fluid or liquid through fluid conductor 101. Examples of conductive fluid include blood or treatment. For example, sensor 110 can sense or detect a corresponding voltage, a corresponding current, and/or a corresponding change in fluid conductivity of the fluid flowing through the fluid conductor 101.

In various embodiments, multiple sensors 110 of same or differing configurations may be employed along the fluid conductor 101 at different positions. Multiple sensors 110 may be employed as part of a failsafe system should one or more of the sensors malfunction. Additionally, multiple sensors 110 may be employed to ensure localized detection. Optionally or alternatively, additional sensors or sensor circuitry 111 can be implemented, which can detect fault conditions or potential fault conditions associated with treatment device 102. Optionally or alternatively, additional sensors or sensor circuitry 112 can be implemented on or with patient 200 to detect fault conditions or potential fault conditions. Optionally or alternatively, adverse or dangerous, or potentially adverse or dangerous conditions may be sensed, detected, or otherwise identified by sensors 110, 111, and 112.

The measured signals may be fed to the controller 104 or a simple circuit. The controller 104 may execute an algorithm or the simple circuit can detect a threshold signal level, which may indicate the detected electrical signal is at or above a predetermined threshold. In various embodiments, the predetermined threshold can be based on a minimum level of current capable of causing physiological damage to the patient and/or in accordance with a governmental standard patient leakage current value.

In various embodiments, the system may be equipped with an electro-mechanical means 106, such as a valve or a fluid isolation actuator, to interrupt the conductive fluid path as commanded by output signal(s) from controller 104. The output signal(s) from the controller 104 can be based on the sensed or detected electrical signal from the one or more sensors 110, 111, and/or 112. Once the controller 104 identifies a triggering condition, it can command the electro-mechanical device 106 to interrupt the fluidic path to prevent an unacceptable or undesirable electric current flow to and/or through the patient 200. In various embodiments, multiple electro-mechanical devices 106 of same or differing configurations may be employed along the fluid conductor 101 at different positions. Interruption of the fluid path can include rerouting of the fluid such that fluid no longer flows to the patient 200.

The 110 sensor can be constructed in such a way that it has a relatively high level of electrical impedance to the patient 200, medical device electric circuit, AC Mains, and electrical ground. Such construction can prevent the sensor 110 from creating additional patient leakage current. If the sensor 110 entails inducing an electric signal (voltage or current) into a patient 200 to perform the measurement, such as patient impedance to earth measurement, the excitation measurement signal levels should not create any or any unacceptable patient leakage current.

In addition, the sensor 110 can be placed relatively closer to the patient connection on the fluidic line 101 than the electro-mechanical device 106. Such a configuration can allow monitoring of patient condition, while the fluid line 101 is not connected to the patient 200 during the system startup or after a protection circuit goes off. Optionally, placing sensor 110 further away from the patient connection than the electro-mechanical device 106 may be required if the sensor design does not meet certain electrical insulation impedance requirements. In this case the controller 104 can have a software-, hardware-, or combination software/hardware-implemented resettable latch that can latch an alarm condition, and that may be reset by means other than a signal of the sensor 110 to allow the treatment device 102 operation to resume once the dangerous condition has been cleared. For example, reset may be accomplished by a manual control to ensure the problem has been acknowledged by an operator.

Figure 4:
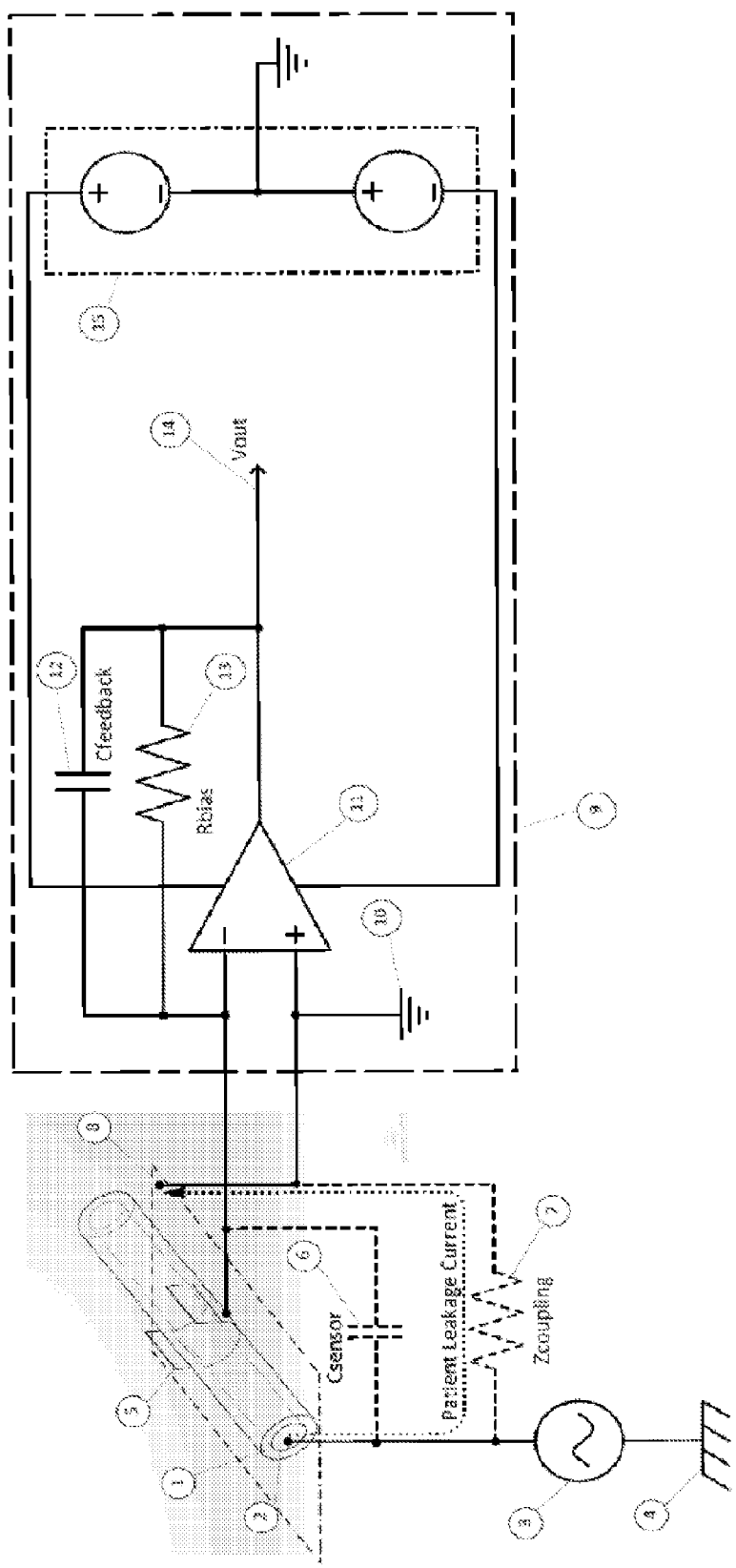
FIG. 4 shows diagrammatic and schematic portions of a system according to one or more embodiments of the disclosed subject matter.

FIG. 4 shows an example of sensor 110 from FIG. 3. Specifically, FIG. 4 shows a non-invasive capacitive voltage sensor that can be used to measure the voltage drop created by the patient leakage current across impedance Zcoupling. Non-conductive tube 1 contains conductive fluid 2 flowing to the patient applied part (not shown on the drawing). Voltage source 3, which can represent voltage created by an external source that the patient touches, may be connected (i.e., capacitively coupled) to fluid 2. The patient leakage current path is created by the coupling impedance Zcoupling 7 between conductive fluid 2 and a conductive part 8 of the medical apparatus adjacent to tube 1. Conductive part 8 can be connected to earth 4 (though not necessarily directly). A capacitive sensor 6 comprising a u-shaped conductive electrode 5 with tube 1 inserted in it, for example, has an equivalent capacitance Csensor 6 between conductive fluid 2 and electrode 5. Electronic circuit 9 can condition and amplify the capacitive sensor output signal and generate output signal Vout 14, which can be fed to a controller (e.g., 104 in FIG. 3) that compares it to a predetermined threshold value (e.g., a safe threshold value or a threshold value in accordance with a Standard) and makes the decision when to activate the mechanism (e.g., electro-mechanical device 106 in FIG. 3) to stop fluid flow to the patient. Electronic circuit 9 may be constructed and operative as an inverting amplifier based on operational amplifier 11 fed by bipolar isolated DC power supply 15. A value of feedback capacitor Cfeedback 12 impedance may be much lower in the frequency range of interest than the value of bias resistor Rbias 13. Bias resistor 13 can serve the purpose of returning the bias current of operational amplifier 11 inverting input. Electronic circuit 9 can have an isolated ground plane 10 that is connected to the conductive part 8 of the medical apparatus. The following equation can represent the relationship between Vout 14 and patient leakage current designated as Ileak:

$$V_{out} = I_{leak} * Z_{coupling} * (C_{sensor}/C_{feedback})$$

Accordingly, electronic circuit 9 can measure patient leakage current, as described by the equation above, in the event when patient leakage current is induced by the voltage source within a medical apparatus and flows into an earthed patient. In this case, the voltage source will be connected to a conductive part 8 of the medical apparatus (not necessarily directly) and conductive fluid 2 will be connected to earth 4 through the patient impedance.

Figure 5:
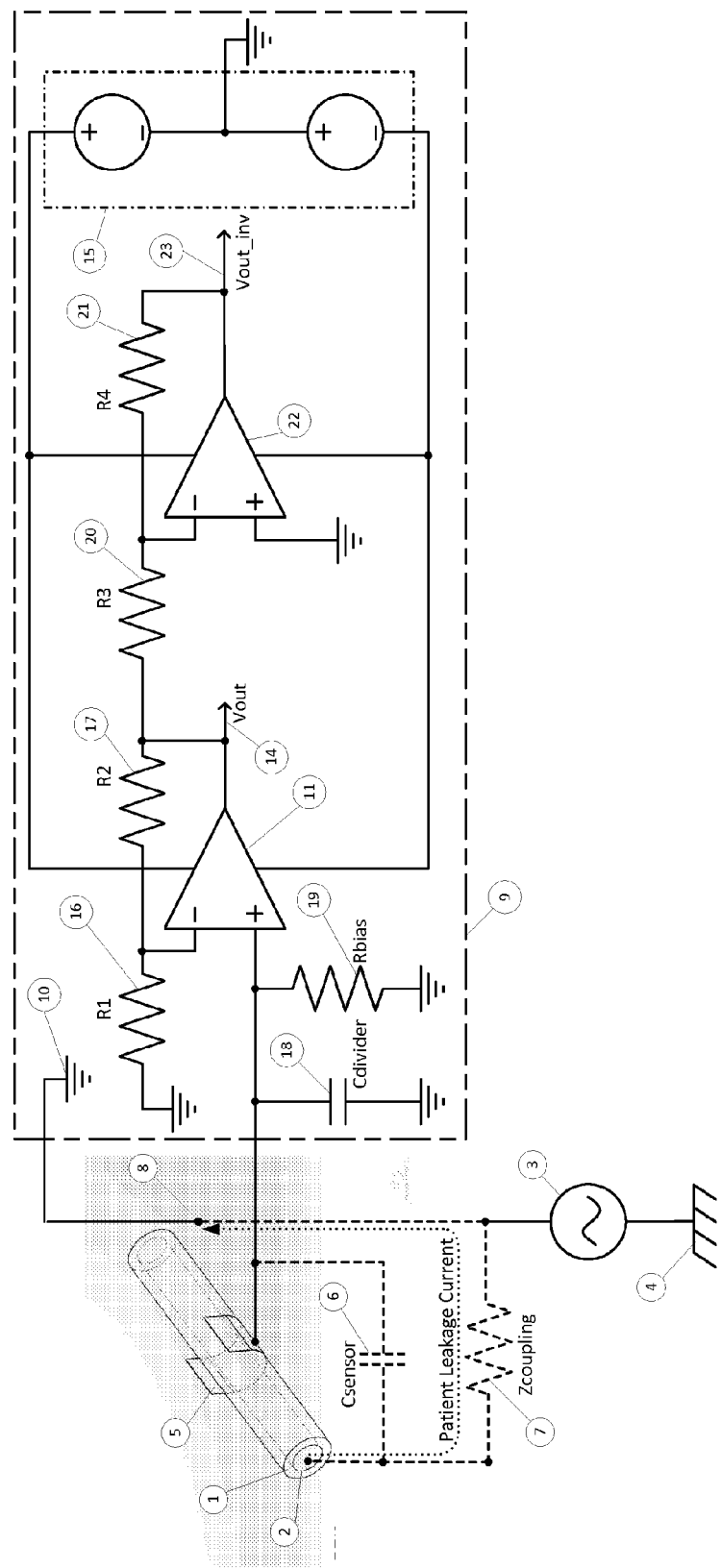
FIG. 5 shows diagrammatic and schematic portions of a system according to one or more embodiments of the disclosed subject matter.

FIG. 5 shows another possible implementation of an electronic circuit 9 for a non-invasive capacitive voltage sensor that can be used to measure the voltage drop created by the patient leakage current across impedance Zcoupling. Similar to FIG. 4, non-conductive tube 1 can contain conductive fluid 2 flowing to the patient applied part (not shown). A capacitive sensor comprising a u-shaped conductive electrode 5 with tube 1 inserted in it can be provided and can have an equivalent capacitance Csensor 6 between conductive fluid 2 and electrode 5. Voltage source 3, representing voltage created inside the medical electrical fluid handling device, is shown connected to a conductive part 8 of the medical apparatus. The patient leakage current path is created by the coupling impedance Zcoupling 7 between conductive fluid 2 and conductive part 8 of the medical apparatus adjacent to tube 1. Incidentally, patient isolation impedance to earth is not shown. Electronic circuit 9 can condition and amplify the capacitive sensor output signal and can generate output signals Vout 14 and Vout_inv 23 fed into a controller (e.g., 104 in FIG. 3) that can compare the values to a predetermined threshold value (e.g., a safe threshold value or a threshold value in accordance with a Standard) and makes the decision when to activate the protection mechanism (e.g., electro-mechanical device 106 in FIG. 3) to stop fluid flow to the patient. Electronic circuit 9 can output both inverted and non-inverted signals so that a comparator in the controller can react to either positive or negative half wave of the AC voltage signal so as to speed up the response time to a potential or real patient leakage current situation. Electronic circuit 9 can be constructed and operative as a non-inverting amplifier based on operational amplifier 11 fed by bipolar isolated DC power supply 15. The value of divider capacitor Cdivider 18 impedance may be much lower in the frequency range of interest than the value of bias resistor Rbias 19. A capacitive divider formed by the equivalent sensor capacitance Csensor 6 and capacitor Cdivider 18 can bring the circuit input signal within the working range of amplifier 11. Bias resistor 19 can serve the purpose of returning the bias current of operational amplifier 11 to non-inverting input. Electronic circuit 9 can have an isolated ground plane 10 connected to the conductive part 8 of the medical apparatus. The following equation can represent the relation between Vout 14 and patient leakage current designated as $I_{leak}$:

$$V_{out} = I_{leak} * Z_{coupling} * (1+R2/R1) * (C_{sensor}/(C_{sensor} + C_{divider}))$$

Inverting amplifier 22 can be formed by operational amplifier 22 and resistors 20 and 21. Resistors 20 and 21 may be equal.

Sensor performance can be verified by the medical device during a power-on self-test, for example, before the medical device is connected to a patient, by providing another u-shaped electrode coupled to the tube and applying the AC voltage to it sufficient to trip the protection circuit. The sensing circuit should detect this voltage and activate the protection mechanism (e.g., electro-mechanical device 106 in FIG. 3).

In the case of voltage detection corresponding to patient leakage current, detected voltage may approach and possibly reach or exceed the level calculated by the following formula:

$$V_{trip} = I_{leak\ limit} * Z_{coupling},$$

where $V_{trip}$=controller High Limit Alarm Voltage triggering shutoff referenced to Earth; $I_{leak\ limit}$=Patient Leakage Current Limit, defined by a medical equipment safety standard, for example; and $Z_{coupling}$=coupling impedance between fluid flowing to the patient applied parts and medical fluid handling apparatus electrically conductive components.

When the detected voltage has reached, is within a certain value from the predetermined voltage level $V_{trip}$, or exceeds the predetermined voltage level $V_{trip}$, a (e.g., controller 104) can provide control signal(s) to cause electro-mechanical device(s) as set forth herein to disconnect the patient fluidic connection, thus preventing any current, an undesirable amount of current, or an excessive amount of current from reaching and passing through the patient. The treatment device can be thereafter or simultaneously put in a standby mode or turned off, for instance, until it is determined that a safe condition exits (i.e., no or a suitable amount of leakage current). Thus, the system can protect the patient from being subjected to any current, an undesirable amount of current, or an excessive amount of current created by voltages both internal to the system and applied to the patient externally.

Optionally, embodiments can include at least two measurement devices: a first measurement device measuring the impedance between patient and Earth, and a second measurement device measuring electric voltage applied to the patient with respect to earth. The controller 104 can calculate patient leakage current using the following formula:

$$I_{patient\ leak} = V_{patient}/Z_{coupling},$$

where $I_{patient\ leak}$=Patient leakage current, as calculated by the controller, for example; $V_{patient}$=Patient voltage measured with respect to Earth; and $Z_{coupling}$=coupling impedance between fluid flowing to the patient applied parts and medical fluid handling apparatus electrically conductive components.

When calculated leakage current approaches, reaches, or exceeds a limit defined by the standard, for example, a controller can command electro-mechanical device(s) as set forth herein to interrupt the fluid connection to the patient. The treatment device can be thereafter or simultaneously put in a standby mode or turned off, for instance, until it is determined that a safe condition exits (i.e., no or a suitable amount of leakage current).

In one or more embodiments, multiple electric conduction paths may exist in a fluid handling medical apparatus or device connected to a patient. For some such configurations a reliable way to estimate patient leakage current is to measure electric current flowing in the fluidic lines connecting machine or device to the patient. If there are multiple fluidic paths and other connections to the patient the sum of currents measured should be less than the dangerous patient leakage current value. A controller can collect and add the current values measured, compare the sum to the limit, and generate shutoff signals to the electro-mechanical means (e.g., one or more valves associated with each fluidic line) when the sum of currents is over the limit. Optionally, current signals' phases should be accounted for in such calculation. A reliable electric ground may not be available at the installation site. Thus, embodiments according to the disclosed subject matter can provide a patient leakage protection scheme that does not require electrical ground reference connection. So the device or machine can be fed from an AC source without functional or protective earth.

FIGS. 6A and 6B show portions of a capacitive liquid AC voltage sensor according to embodiments of the present invention.

FIG. 6A shows an example of a metal electrode, which can be mounted in a plastic body of a conductor. Such electrode can form part of a capacitive sensor. FIG. 6B can represent a tube to be filled with conductive fluid, such as water, blood, or treatment. The metal electrode can be the dimensions shown in FIG. 6A or other suitable dimensions.

Patient leakage current as a result of the external voltage applied to the patient configuration can be reduced using plastic elements (e.g., plastic plates) in the construction of the medical equipment to reduce the coupling between the conductive fluid flowing through it and conductive components of the medical equipment and an external power supply.

Figure 7:
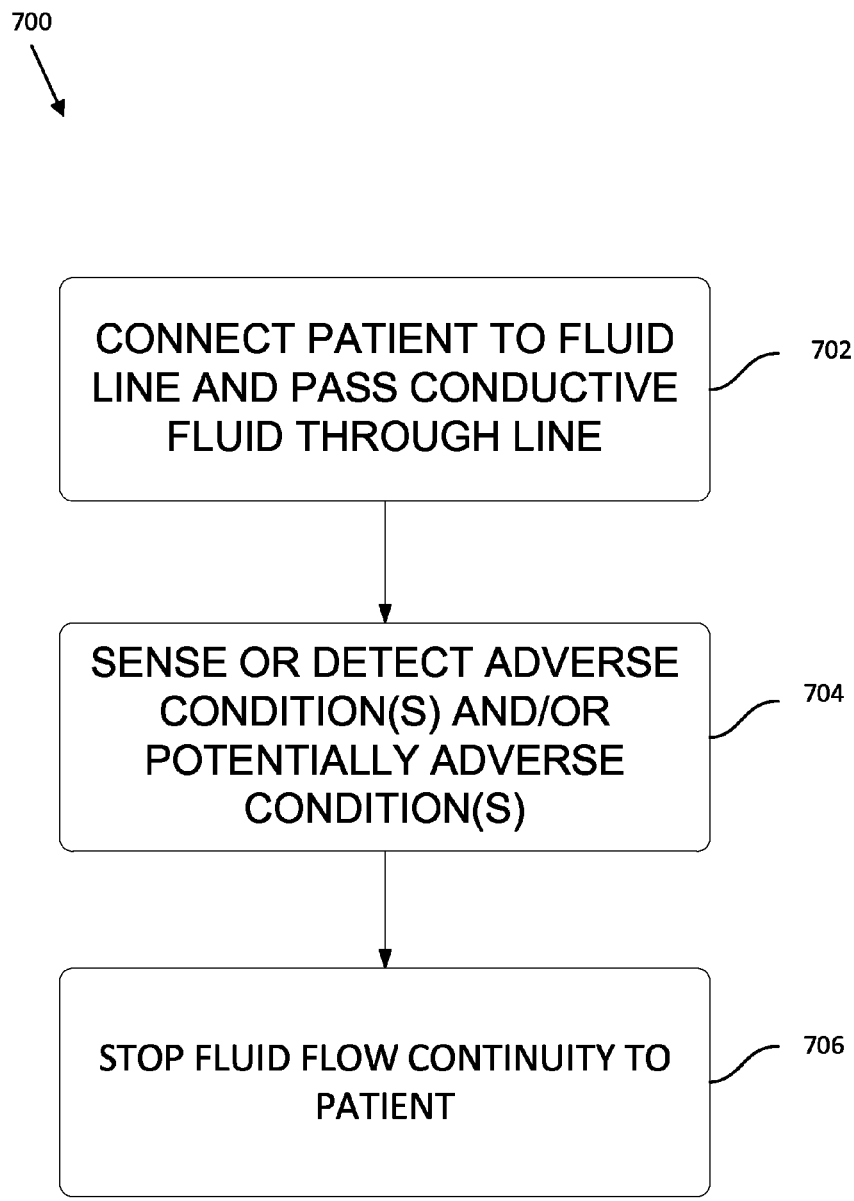
FIG. 7 is a flow chart of a method according to embodiments of the disclosed subject matter.

FIG. 7 is a flow chart of a method 700 according to embodiments of the disclosed subject matter. The method can be to protect an induced electric current, specification, an induced patent leakage current. The provided protection can be before patient leakage current is generated, before it reaches the patient, or after it reaches the patient.

In the method, the patient can be connected to a treatment device via a fluid line. Conductive fluid can be sent from a treatment machine to the patient 702. An adverse or dangerous condition or an anticipated adverse or dangerous condition can be sensed, detected, or otherwise identified 704. Patient leakage current above a predetermined threshold is one example of an adverse or dangerous condition. Responsive to the sensing, detecting, or identifying, the fluid flow to the patient is stopped 706. Stopping fluid flow to the patient can include breaking the fluid conductive path to the patient and/or rerouting the fluid from the patient as shown and described herein.

Although particular configurations have been discussed herein, other configurations can also be employed. It is, thus, apparent that there is provided, in accordance with the present disclosure, medical treatment device electrical safety methods, devices, apparatuses, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

It will be appreciated that portions (including an entire portion) of any modules, processes, methods, and circuitry described above can be implemented in hardware, hardware programmed by software, software instructions stored on a non-transitory computer readable medium or a combination of the above.

Having now described embodiments of the disclosed subject matter, it should be apparent to those skilled in the art that the foregoing is merely illustrative and not limiting, having been presented by way of example only. Numerous modifications and other embodiments (e.g., combinations, rearrangements, etc.) are within the scope of one of ordinary skill in the art and are contemplated as falling within the scope of the disclosed subject matter and any equivalents thereto. It can be appreciated that variations to the disclosed subject matter would be readily apparent to those skilled in the art, and the disclosed subject matter is intended to include those alternatives. Further, since numerous modifications will readily occur to those skilled in the art, it is not desired to limit the disclosed subject matter to the exact construction and operation illustrated and described, and accordingly, all suitable modifications and equivalents may be resorted to, falling within the scope of the disclosed subject matter.

What is claimed is:

1. A method for protecting a patient from an electrical source, comprising:
   connecting the patient to a treatment device by a fluid line;
   receiving a voltage or current signal indicating a flow of current or voltage in the fluid line connected to the patient from a sensor configured to electrically couple to a fluid in the line to detect current or voltage in the fluid at a position in the fluid line proximate to the sensor;
   determining if the voltage or current exceeds a predetermined threshold; and
   in response to the determining, breaking fluid continuity between the patient and the treatment device to halt the flow of current in the fluid carried by the fluid line.

2. The method of claim 1, further comprising generating a human perceptible output indicating the excessive detected voltage or current.

3. A system for protecting a patient from an electrical source, the system comprising:
   a fluid line connected to the patient;
   a sensor configured to electrically couple to a fluid in the fluid line and output a voltage signal or a current signal indicating a flow of current or a voltage in the fluid at a position in the fluid line proximate to the sensor;
   means for determining if the voltage or the current exceeds a predetermined threshold; and
   means for closing a valve to break continuity between the patient and the treatment device and halt the flow of current in the fluid carried by the fluid line in response to the determined voltage or current.

4. The system of claim 3, further comprising means for generating a human perceptible output indicating the excessive detected voltage or current.

5. A system for stopping flow of a conductive fluid to a patient, comprising:
   a sensor configured to be electrically coupled to the conductive fluid in a fluid line identifying an unsatisfactory condition in the system indicative of patient leakage current or anticipated patient leakage current of an unacceptable amount; and
   means for stopping fluid continuity of the conductive fluid in the fluid line from a treatment machine to the patient and halting the flow of current in the fluid line based on the identified unsatisfactory condition.

6. The system according to claim 5, wherein said means for stopping the fluid flow continuity to the patient mechanically interrupts the fluid conductive path to the patient.

7. The system according to claim 5, wherein said means for stopping the fluid flow continuity to the patient includes a pinching apparatus that pinches closed a corresponding fluid flow line.

8. The system according to claim 5, wherein said means for stopping the fluid flow continuity to the patient includes a valve to divert flow to a circuit having an air break.

9. The system according to claim 8, wherein the circuit has a drip chamber.

10. The system according to claim 5, wherein the unsatisfactory condition is one or more of a sensed patient leakage current exceeding a predetermined amount, a sensed voltage differential associated with the patient leakage current exceeding a predetermined amount, a fault condition, an anticipated fault condition, a sensed change in fluid conductivity, a disconnection from ground, and vibration.

11. The system according to claim 5, wherein the fluid continuity is temporarily interrupted without shutting down a means for supplying conductive fluid to the patient, wherein, once the unsatisfactory condition is resolved, the fluid continuity to the patient is restored.

12. The system according to claim 5, wherein the acceptable amount of patient leakage current is zero.

13. The system according to claim 5, wherein the acceptable amount of patient leakage current is 10 µA or below 10 µA.

14. The system according to claim 5, wherein said means for stopping fluid continuity to the patient causes reduction of patient leakage current to keep within or reduce to an acceptable limit.

15. The system according to claim 5, wherein unsatisfactory condition is a fault condition.

16. The system according to claim 5, wherein the system is operative to stop fluid continuity to the patient when a fluid treatment machine thereof sinks to earth patient leakage current caused by external voltage applied to the patient.

17. The system according to claim 5, further comprising means for handling fluid coupled to the patient via one or more patient fluid flow lines, wherein normal operation of said fluid handling means is interrupted responsively to the unsatisfactory condition indication.

18. The system according to claim 5, wherein the unsatisfactory condition indication is predictive of a harmful, dangerous, or adverse situation to the patient.

19. The system according to claim 5, wherein said means for stopping fluid continuity to the patient includes redundant devices of same or different types for stopping fluid continuity.

20. The system according to claim 5, wherein stopping fluid continuity to the patient prevents or stops electric shock to the patient.

21. The system according to claim 5, wherein said means for identifying an unsatisfactory condition in the system includes
   one or more of at least one sensor disposed external to means for handling fluid and operative to sense a characteristic of a fluid line providing the conductive fluid to the patient;
   at least one sensor disposed internal to said means for handling fluid and operative to sense a characteristic of said means for handling fluid indicative of patient leakage current or an anticipated occurrence of patient leakage current; and at least one sensor disposed on or in association with the patient to sense indications of patient leakage current or an anticipated occurrence of patient leakage current.

22. The system according to claim 5, wherein said means for stopping the fluid flow continuity to the patient includes a valve to break continuity between the patient and a treatment device.

23. The system according to claim 5, wherein said means for stopping the fluid flow continuity to the patient includes a folding apparatus to fold the tube to close the corresponding fluid flow line.

24. The system according to claim 5, wherein said means for stopping the fluid flow continuity to the patient includes a bubble introducing apparatus to introduce air into the fluid flow line to form an air break.

25. The system according to claim 5, wherein said sensor is a capacitive sensor.

* * * * *